(12) United States Patent
Asai et al.

(10) Patent No.: US 8,764,703 B2
(45) Date of Patent: Jul. 1, 2014

(54) PRE-FILLED SYRINGE

(75) Inventors: Takashi Asai, Osaka (JP); Tsutomu Takahashi, Osaka (JP); Kenyu Ito, Osaka (JP); Atsushi Ishikawa, Osaka (JP)

(73) Assignee: Nipro Corporation, Osaka-shi (JP)

( * ) Notice: Subject to any disclaimer, the term of this patent is extended or adjusted under 35 U.S.C. 154(b) by 0 days.

(21) Appl. No.: 13/703,319

(22) PCT Filed: Jun. 8, 2011

(86) PCT No.: PCT/JP2011/063116
§ 371 (c)(1),
(2), (4) Date: Dec. 10, 2012

(87) PCT Pub. No.: WO2011/155517
PCT Pub. Date: Dec. 15, 2011

(65) Prior Publication Data
US 2013/0090596 A1 Apr. 11, 2013

(30) Foreign Application Priority Data
Jun. 11, 2010 (JP) .................................. 2010-134505

(51) Int. Cl.
*A61M 37/00* (2006.01)
(52) U.S. Cl.
USPC ............................................ 604/90; 604/230
(58) Field of Classification Search
USPC ............................................ 604/89–91, 230
See application file for complete search history.

(56) References Cited

U.S. PATENT DOCUMENTS

| 5,290,228 A * | 3/1994 | Uemura et al. ................. 604/90 |
| 2007/0161961 A1 | 7/2007 | Hasegawa |
| 2008/0234632 A1 | 9/2008 | Hasegawa |
| 2010/0106086 A1 | 4/2010 | Sudo et al. |
| 2010/0262074 A1 * | 10/2010 | Seiferlein et al. ............... 604/89 |

FOREIGN PATENT DOCUMENTS

| EP | 0 879 611 A2 | 11/1998 |
| EP | 1 674 121 A1 | 6/2006 |
| EP | 1 728 528 A1 | 12/2006 |
| EP | 1 808 192 A1 | 7/2007 |
| JP | 6-142203 A | 5/1994 |
| JP | 2007-185319 A | 7/2007 |
| JP | 2009-61343 A | 3/2009 |
| WO | WO 2005/089837 A1 | 9/2005 |
| WO | WO 2008/156216 A1 | 12/2008 |

OTHER PUBLICATIONS

JP 2009061343 Machine Translation. Mar. 26, 2009.*

* cited by examiner

*Primary Examiner* — Nathan R Price
(74) *Attorney, Agent, or Firm* — Birch, Stewart, Kolasch, & Birch, LLP

(57) ABSTRACT

In a pre-filled syringe having an intermediate gasket, a liquid drug is enclosed in the second chamber located on the base end side with respect to the intermediate gasket while a powdered drug is enclosed in the first chamber located on the front end side with respect to the intermediate gasket. The intermediate gasket has at least two layers including a front end layer corresponding to a wall of the first chamber and a base end layer corresponding to a wall of the second chamber, and also has a low water-absorptive layer in the layer on the base end side with respect to the front end layer. The base end layer is formed of a material having low water-absorptivity and not lowering a pH of the liquid drug.

6 Claims, 3 Drawing Sheets

PRE-FILLED SYRINGE

TECHNICAL FIELD

The present invention relates to a pre-filled syringe. More specifically, the present invention relates to a pre-filled syringe that has separate chambers partitioned therewithin and enclosing a liquid drug and a powdered drug, respectively, and that is suitable for administration of the liquid drug and the powered drug which are mixed, dissolved and suspended in use.

BACKGROUND ART

Conventionally, there is a pre-filled syringe characterized in that a medical drug is enclosed in the syringe in advance. This pre-filled syringe is easy to use since it allows drugs to be administered as they are without having to perform a drug filling operation. Accordingly, this pre-filled syringe is applied to various drugs and widely used.

In addition to such a type of pre-filled syringe enclosing only a liquid drug, there is also a pre-filled syringe, as disclosed in WO/2005/089837, that has separate chambers partitioned therewithin and enclosing a liquid drug and a powdered drug, respectively, which are in use mixed, dissolved and suspended for administration.

Medical drugs thus stored without being prepared for mixing a liquid drug and a powdered drug are often not suitable to be stored in the prepared state since the drugs may be unstable in the mixed state, and the drugs in contact with moisture for a relatively long period of time may cause defects such as a decrease in titer, deterioration or coagulation of the drugs, which leads to difficulty in distribution of the drugs upon administration.

If a gasket partitioning the internal space into chambers enclosing a liquid drug and a powdered drug, respectively, is highly absorptive, the gasket absorbs the liquid drug (or moisture thereof), to cause the liquid drug to reach the portion corresponding to the wall of the powered drug chamber, with the result that the powdered drug and the liquid drug may be brought into contact with each other. Furthermore, if the powdered drug is unstable to moisture, also when the portion of the gasket corresponding to the wall of the powdered drug chamber is not dry, the powdered drug may come into contact with moisture due to the moisture remaining in the gasket.

In order to solve the problem caused by the moisture contained in the powdered drug chamber, the invention disclosed in Japanese Patent Laying-Open No. 6-142203 is proposed. According to this, for the purpose of preventing the moisture remaining due to sterilization by steam from affecting the powdered drug, the intermediate gasket is formed of two members, and one of the members located closer to the powdered drug chamber is fully dried and inserted after sterilization by steam, thereby preventing moisture from remaining in the powdered drug chamber.

CITATION LIST

Patent Literature

PTL 1: WO/2005/089837
PTL 2: Japanese Patent Laying-Open No. 06-142203

SUMMARY OF INVENTION

Technical Problem

According to the pre-filled syringe disclosed in the foregoing prior art literatures, essentially, when a plunger is pressed toward the end, an intermediate gasket is moved into a region of the barrel having a bypass formed therein, to transfer the entire liquid drug to the first chamber while bringing the intermediate gasket and the base end gasket into contact with each other (preparation (inter-chamber communication) operation). When the plunger is further pressed, the intermediate gasket passes through the region of the barrel having a bypass formed therein, so that the liquid drug can be injected.

In order to prevent moisture from affecting a powdered drug, the powdered drug only has to be kept out of contact with the gasket in contact with a liquid. Accordingly, by employing an approach of forming an intermediate gasket as disclosed in PTL 2 using two members to prevent the powdered drug and the gasket in contact with a liquid from coming into contact with each other, moisture can be prevented from contacting the powdered drug irrespective of the material properties of the gasket. However, if the intermediate gasket is formed of two members (on the front end side and the rear end side) as disclosed in PTL 2, during the drug preparation operation, movement of the intermediate gasket into the region of the barrel having a bypass formed therein causes the liquid drug to be introduced between these two members of the intermediate gasket. Then, the intermediate gasket on the front end side is pressed toward the front end by inflow of the liquid solution, thereby reaching the front end side of the bypass, so that the intermediate gasket on the front end side blocks the bypass. This may cause a serious problem that the entire amount of the liquid drug cannot be transferred to the first chamber, and therefore, drug preparation cannot be made.

In addition, since the material of the gasket forming a part of a storage container is, similarly to this container, kept in contact with a plurality of drugs due to storage and the like, a material suitable to each drug (not altering the quality) should be selected. Since the material at least comes into contact with the powdered drug, it should surely be low water-absorptive. In addition to this, special care should be taken in selecting the material because a liquid drug may undergo a pH change due to the influence of the rubber material in contact therewith. Furthermore, the material should be excellent also in slidability and fluid-tightness.

The present invention aims to provide a pre-filled syringe having an intermediate gasket that is substantially formed of a single member, excellent in slidability and fluid-tightness, low water-absorptive, and less influential on the pH of the liquid drug.

The present inventors have thus found that a pre-filled syringe described below is employed for providing an intermediate gasket having required characteristics obtained by assembling a plurality of materials in layers in the axial direction, and consequently, have achieved the invention of the present application. The pre-filled syringe includes a barrel having a front end at which an injection needle connection portion is formed and a base end provided with an opening; a base end gasket fluid-tightly and slidably inserted into the barrel; a plunger provided with a plunger rod on a base end side of the base end gasket; an intermediate gasket fluid-tightly and slidably inserted on a front end side of the base end gasket and dividing an inside of the barrel into a first chamber and a second chamber; and a bypass circuit protruding in a radially outward direction of the barrel and formed longer than an effective seal length of the intermediate gasket with respect to an axial direction of the barrel. A liquid drug is enclosed in the second chamber surrounded by the intermediate gasket and the base end gasket in the barrel, and a powdered drug is enclosed in the first chamber on a front end side of the barrel with respect to the intermediate gasket. The intermediate gasket has at least two layers including a front end layer corresponding to a wall of the first chamber and a base end layer corresponding to a wall of the second chamber, and has at least a low water-absorptive layer in a layer on the base end side with respect to the front end layer. The base end layer is formed of a material having low water-absorptivity and not lowering a pH of the liquid drug.

Specifically, it is possible to block moisture from the liquid drug by the base end layer of the gasket, thereby preventing changes in qualities of the liquid drug and the powdered drug.

The front end layer may be formed of a material having low water-absorptivity.

An intermediate layer may be formed between the front end layer and the base end layer.

The front end layer may be formed of chlorinated butyl rubber or brominated butyl rubber, and the base end layer may be formed of normal butyl rubber.

Furthermore, the pre-filled syringe may be configured such that a front end gasket is fluid-tightly and slidably inserted into a front end within a barrel, to form a first chamber in a space within the barrel surrounded by the front end gasket and the intermediate gasket; and at the front end of the barrel, a nozzle member is provided that includes an injection needle connection portion formed at a front end, a front end gasket housing portion in which the front end gasket can be housed at a base end, and a liquid flow path formed therein that extends on an inner circumferential wall in an axial direction. Through this liquid flow path, a liquid drug can pass when the front end gasket is housed in the front end gasket housing portion. An injection needle may be attached to the injection needle connection portion in advance.

Advantageous Effects of Invention

Since the pre-filled syringe of the present invention includes an intermediate gasket that prevents a pH change of the liquid drug and contact of moisture with a powdered drug during storage, this pre-filled syringe can maintain the drug storage state excellently, can be excellent in use, and therefore, suitably applied to medical procedure.

DESCRIPTION OF EMBODIMENTS

Figure 1:
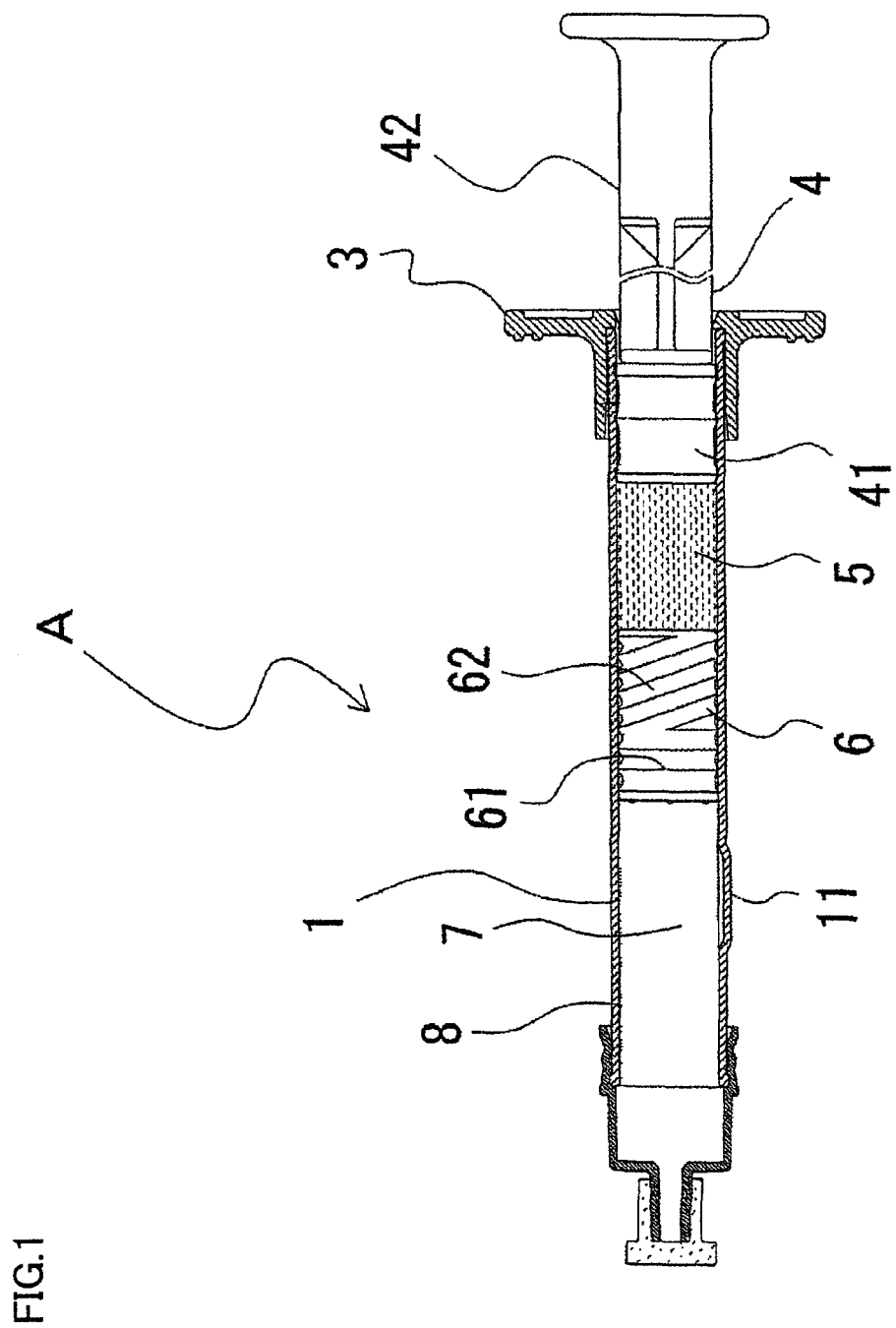
FIG. 1 is a longitudinal cross-sectional view of one embodiment of a pre-filled syringe according to the present invention.

A pre-filled syringe of the present invention will be hereinafter described with reference to the drawings. It is to be noted that the invention of the present application is not limited to embodiments illustrated in the drawings.

Figure 2:
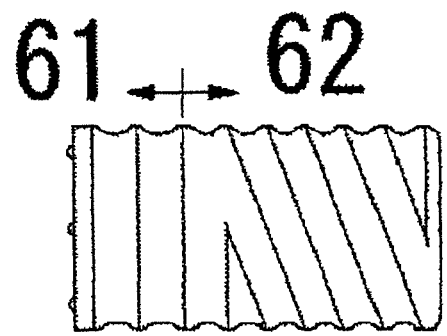
FIG. 2 is a side view of an intermediate gasket of the pre-filled syringe shown in FIG. 1.
Figure 3:
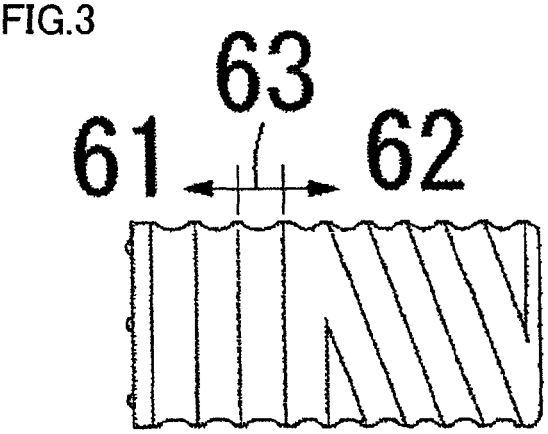
FIG. 3 is a side view of one embodiment of the intermediate gasket having an intermediate layer in the pre-filled syringe according to the present invention.

FIG. 1 is a longitudinal cross-sectional view of one embodiment of a rubber plug for a dropping container vial of a liquid drug container according to the present invention. FIG. 2 is a longitudinal cross-sectional view of another embodiment of a pre-filled syringe according to the present invention. FIG. 3 is a side view of one embodiment of an intermediate gasket of the pre-filled syringe according to the present invention.

A pre-filled syringe A of the present invention will be described with reference to FIG. 1 by way of example. A barrel 1 has an injection needle connection portion 24 on its front end side. Almost in the middle portion of barrel 1, a bypass portion 11 is formed that protrudes along the axis in the radially outward direction. Barrel 1 also has an opening at its base end that is provided with a flange 3. A base end gasket 41 is fluid-tightly and slidably housed within barrel 1 and has a base end to which a plunger rod 42 is connected (base end gasket 41 and plunger rod 42 form a plunger 4). Within barrel 1, an intermediate gasket 6 is fluid-tightly and slidably housed on the base end side with respect to bypass 11, and partitions the space within the barrel. A powdered drug D is contained in the space (first chamber 7) on the front end side with respect to the intermediate gasket within the barrel while a liquid drug L is contained in the space (second chamber 5) surrounded by the intermediate gasket and the base end gasket within the barrel. A rubber cap 9 is attached to injection needle connection portion 24, thereby bringing first chamber 7 into a sealed state.

As shown in FIG. 2, intermediate gasket 6 is formed of a seal portion 61 in the front end layer and a spiral groove portion 62 in the base end layer. The front end layer is made of chlorinated butyl rubber while the base end layer is made of normal butyl rubber. Chlorinated butyl rubber and normal butyl rubber are preferable since chlorinated butyl rubber has excellent sealing property and slidability while normal butyl rubber has low water-absorptivity and a neutral property.

Intermediate gasket 6 has an effective seal length corresponding to a portion in which fluid-tightness is substantially maintained at the sliding surface between barrel 1 and intermediate gasket 6. In the case of FIG. 2, this effective seal length corresponds to an axial length of a diagonally lined area in intermediate gasket 6 (for example, fluid-tightness in spiral groove portion 62 is not maintained since a liquid enters spiral groove portion 62 by pressure of a plunger).

Chlorinated butyl rubber serving as a front end layer and having an excellent sealing property and slidability is preferably employed since it additionally has low water-absorptivity. However, since rubber itself is acid, it is not preferable to provide the rubber at the position where it contacts a liquid drug for a relatively long period of time when this liquid drug is neutral or alkaline. Accordingly, by forming the base end layer with normal butyl rubber that is low water-absorptive and neutral, an intermediate gasket having a configuration suitable to contact with such liquid drugs is achieved.

Since it is difficult to lower permanent strain of normal butyl rubber, this normal butyl rubber tends to show relatively high sliding resistance. For example, normal butyl rubber only has to be formed so as to maintain the sealing property to such an extent that a liquid drug is not directly in contact with the front end layer, while substantial slidability only has to be achieved by chlorinated butyl rubber serving as a front end layer. In other words, the slidability only has to be achieved by one of the front end layer and the base end layer (the one superior in properties).

The communication mechanism consisting of an intermediate gasket and a bypass may have not only the structure as shown in FIG. 1, but also the configuration as disclosed in the aforementioned PTL 1, for example, including the general configuration in which a bypass longer than the axial length of the gasket is provided in the barrel. In this case, it is necessary to provide a layer configuration for the gasket such that liquid drug L is out of contact with at least the front end layer during storage.

Although the combination of front end layer 61 and base end layer 62 in the intermediate gasket as described above is merely by way of example, an intermediate layer 63 excellent in slidability and sealing properties may be provided as shown in FIG. 3, to configure the front end layer and the base end layer in consideration only of the suitability to the drugs in contact therewith. Alternatively, if a suitable rubber material having low water-absorptivity cannot be used in terms of the liquid drug in contact therewith, intermediate layer 63 can also be formed with rubber having low water-absorptivity. Intermediate layer 63 may be formed of two or more layers, if necessary.

The above-described intermediate gasket 6 can be fabricated, for example, by introducing material into each part and conducting simultaneous molding. Alternatively, the method of connecting each layer to form one member may be employed, for example, layers may be coupled to one another by screwing in of a screw or by wedge fitting, and thus, the coupled layers only have to serve as substantially one member without being separated from each other during storage and use.

The front end layer of the intermediate gasket is preferably fully dried. Also, it is preferable that the material itself is low water-absorptive since it can further prevent moisture transmission.

Figure 4:
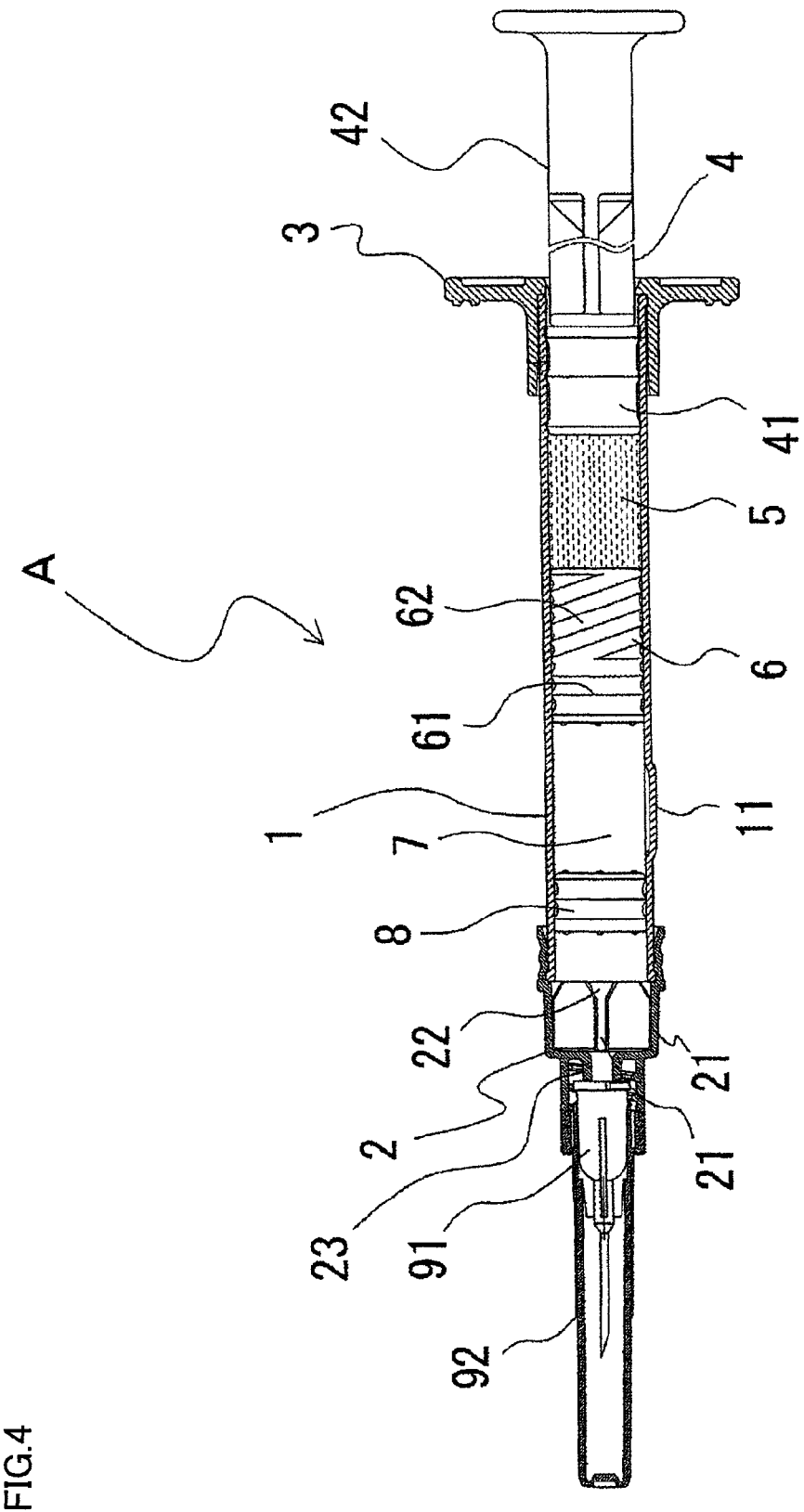
FIG. 4 is a longitudinal cross-sectional view of another embodiment of the pre-filled syringe according to the present invention.

Furthermore, pre-filled syringe A of the present invention is effective for a pre-filled syringe to which a needle is connected in advance, as shown in FIG. 4. In such a pre-filled syringe, an injection needle connection portion is not disposed in barrel 1 itself, but a front end gasket 8 is fluid-tightly and slidably disposed at the front end within approximately cylindrical barrel 1, thereby forming first chamber 7 in the sealed state. At the front end of the barrel, a nozzle member 2 is provided that includes an injection needle connection portion 23 at a front end; a front end gasket housing portion 22 in which a front end gasket can be housed at a base end; and a liquid flow path 21 formed therein that extends on the inner circumferential wall in the axial direction. Through this liquid flow path 21, a liquid drug can flow when the front end gasket is housed in the front end gasket housing portion. An injection needle 91 is connected to the injection needle connection portion and capped by a protector 92.

Similarly to the pre-filled syringe shown in FIG. 1, a cap 9 may be fit to the injection needle connection portion of the pre-filled syringe as shown in FIG. 2, without connecting a injection needle thereto in advance.

INDUSTRIAL APPLICABILITY

As described above, since the pre-filled syringe of the present invention includes an intermediate gasket that prevents a pH change of a liquid drug and contact of moisture with a powdered drug during storage, this pre-filled syringe can maintain the drug storage state excellently, can be excellent in use, and therefore, suitably applied to medical procedure.

REFERENCE SIGNS LIST 1 barrel, 11 bypass, 2 nozzle member, 21 liquid flow path, 22 front end gasket housing portion, 23 injection needle connection portion, 3 flange, 4 plunger, 41 base end gasket, 42 plunger rod, 5 second chamber, 6 intermediate gasket, 61 front end layer, 62 base end layer, 63 intermediate layer, 7 first chamber, 8 front end gasket, 9 cap, 91 injection needle, 92 protector.

The invention claimed is:

1. A pre-filled syringe comprising:
a barrel having a front end at which an injection needle connection portion is formed and a base end provided with an opening;
a base end gasket fluid-tightly and slidably inserted on a base end side within said barrel;
a plunger provided with a plunger rod on a base end side of the base end gasket;
an intermediate gasket fluid-tightly and slidably inserted on a front end side of the base end gasket and dividing an inside of the barrel into a first chamber and a second chamber; and
a bypass circuit protruding in a radially outward direction of the barrel and formed longer than an effective seal length of the intermediate gasket with respect to an axial direction of the barrel, wherein
a liquid drug is enclosed in said second chamber surrounded by said intermediate gasket and said base end gasket in said barrel,
a powdered drug is enclosed in said first chamber on a front end side of said barrel with respect to said intermediate gasket,
said intermediate gasket has at least two layers including a front end layer corresponding to a wall of said first chamber and a base end layer corresponding to a wall of said second chamber, and
said front end layer is formed of chlorinated butyl rubber or brominated butyl rubber, and said base end layer is formed of normal butyl rubber.

2. The pre-filled syringe according to claim 1, wherein said front end layer is formed of a material having low water-absorptivity.

3. The pre-filled syringe according to claim 2, wherein an intermediate layer is formed between said front end layer and said base end layer.

4. A pre-filled syringe comprising:
a barrel having a front end and a base end, each of which is provided with an opening;
a front end gasket fluid-tightly and slidably inserted into the front end within said barrel;
a nozzle member provided at the front end of said barrel, said nozzle member including an injection needle connection portion formed at a front end, a front end gasket housing portion in which said front end gasket can be housed at a base end, and a liquid flow path formed therein that extends on an inner circumferential wall in an axial direction, a liquid drug being able to pass through the liquid flow path when said front end gasket is housed in said front end gasket housing portion;
a base end gasket fluid-tightly and slidably inserted on a base end side within said barrel;
a plunger provided with a plunger rod on a base end side of the base end gasket;
an intermediate gasket fluid-tightly and slidably inserted on a front end side of the base end gasket and dividing an inside of the barrel into a first chamber and a second chamber; and
a bypass circuit protruding in a radially outward direction of the barrel and formed longer than an effective seal length of the intermediate gasket with respect to the axial direction of the barrel, wherein a liquid drug is enclosed in said second chamber surrounded by said intermediate gasket and said base end gasket in said barrel, a powdered drug is enclosed in said first chamber surrounded by said intermediate gasket and said front end gasket in said barrel, said intermediate gasket has at least two layers including a front end layer corresponding to a wall of said first chamber and a base end layer corresponding to a wall of said second chamber, and said front end layer is formed of chlorinated butyl rubber or brominated butyl rubber, and said base end layer is formed of normal butyl rubber.

5. The pre-filled syringe according to claim 4, wherein said front end layer is formed of a material having low water-absorptivity.

6. The pre-filled syringe according to claim 5, wherein an intermediate layer is formed between said front end layer and said base end layer.

* * * * *